United States Patent
Tsujii

(10) Patent No.: US 7,295,690 B2
(45) Date of Patent: Nov. 13, 2007

(54) IMAGE PROCESSING METHOD AND APPARATUS

(75) Inventor: Osamu Tsujii, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 676 days.

(21) Appl. No.: 10/853,978

(22) Filed: May 25, 2004

(65) Prior Publication Data

US 2004/0240717 A1 Dec. 2, 2004

(30) Foreign Application Priority Data

May 27, 2003 (JP) .............................. 2003-149567

(51) Int. Cl.
*G06K 9/00* (2006.01)

(52) U.S. Cl. .................... 382/128; 370/21; 250/363.04

(58) Field of Classification Search ................ 382/128, 382/129, 130, 131, 132, 133, 134, 162, 168; 370/4, 21, 23, 24, 25, 26, 27, 901; 250/363.04
See application file for complete search history.

(56) References Cited

U.S. PATENT DOCUMENTS 6,944,330 B2 * 9/2005 Novak et al. ................ 382/162
2002/0028008 A1 * 3/2002 Fan et al. .................... 382/131

OTHER PUBLICATIONS

Okamura et al, "Computer-Aided Diagnosis System for Lung Cancer Screening through CT", Journal of☐☐Computer Aided Diagnosis of Medical Images, vol. 2, No. 3, Jul. 1998.*

Okamura et al, "Computer-Aided Diagnosis System for Lung Cancer Screening through CT", Journal of Computer Aided Diagnosis of Medical Images, vol. 2, No. 3, Jul. 1998 in Japanese with English Abstract; See p. 14 of specification.

* cited by examiner

*Primary Examiner*—Samir Ahmed
*Assistant Examiner*—Ehsan D Mafi
(74) *Attorney, Agent, or Firm*—Morgan & Finnegan, LLP

(57) ABSTRACT

In step S1, image data obtained by imaging is input to an image input unit (1). In step S2, the diagnosis result obtained by a doctor using the image data obtained by imaging is input as diagnosis information to a diagnosis information input unit (2). In step S3, a keyword table (7) is searched for a keyword input to the diagnosis information input unit (2) or a diagnosis information analyzing unit (3). In step S4, a parameter determining unit (5) selects an initial value parameter used in an image search unit (4) from an initial value table (8) on the basis of the input keyword. In steps S5 and S6, the image search unit (4) determines the optimization degree of the selected parameter by applying the parameter to the input image on the basis of the area or connectivity of a morbid region, and also extracts a morbid region by using a general computer aided diagnosis technique.

4 Claims, 4 Drawing Sheets

IMAGE PROCESSING METHOD AND APPARATUS

FIELD OF THE INVENTION

The present invention relates to an image processing method and apparatus which process an image of a subject to be imaged which is obtained by CT or MRI in the medical field and, more particularly, to a reporting system and reporting method which use a three-dimensional image as a key image attached to a CT or MRI diagnosis report.

BACKGROUND OF THE INVENTION

The use of spiral CT and multi-slice CT or the development of high-speed MRI has made it possible to instantaneously generate 300 or more images by one imaging operation.

In diagnosing such images, a doctor (diagnostician) such as a radiologist uses a high-speed computer environment and displays a plurality of cross section images while switching them at high speed.

A key image or schema (sketch indicating the relationship between an organ and a lesion) which is referred to by a doctor in charge (a physician or the like) is attached to a diagnosis report from the diagnostician.

All 300 or more images can be attached as key images to the above diagnosis report. In this case, however, a large load is imposed on a network or computer and so high-speed display cannot be done sometimes.

Although important images may be selected, it is a painstaking job for the doctor in charge to select key images from 300 or more images. As a simple method, therefore, such images are sometimes simply subsampled at predetermined intervals to about ⅓. However, simply subsampling images in this manner may also simply subsample important images. This may interfere with understanding by the doctor in charge.

SUMMARY OF THE INVENTION

The present invention has been made in consideration of the above problem, and has as its object to provide an image processing method and apparatus which can search all images for a morbid region on the basis of diagnosis information and select an image or images including the morbid region.

It is another object of the present invention to provide an image processing method and apparatus which can determine a parameter in executing rendering processing for an image on the basis of diagnosis information and generate an image or images including a morbid region from the parameter.

It is still another object of the present invention to provide a reporting system and reporting method which can output an image selected by the above image processing or an image having undergone rendering processing by the image processing, as a diagnosis report, with the image being attached to diagnosis information.

In order to solve the above problem and achieve the above objects, according to the present invention, there is provided an image processing apparatus comprising an image input unit which inputs a plurality of medical images obtained by imaging, an information input unit which inputs diagnosis information associated with the input medical images, a search unit which searches the medical images for a morbid region on the basis of the diagnosis information, and a selecting unit which selects a medical image including the found morbid region from the plurality of medical images.

Preferably, the apparatus further comprises a keyword input unit which inputs a keyword for analysis of the diagnosis information, and a parameter determining unit which determines a parameter for execution of a search by the search unit from the keyword and the diagnosis information.

Preferably, the parameter includes at least one of each CT value/MRI value range for a medical image, each CT value/MRI value range which designates a lesion, and a slice position, and is selected from a table storing initial values thereof by the parameter determining unit.

Preferably, the apparatus further comprises an optimizing unit which optimizes the parameter for the medical image.

In addition, according to the present invention, there is provided an image processing apparatus comprising an image input unit which inputs a plurality of medical images obtained by imaging, an information input unit which inputs diagnosis information associated with the input medical images, a rendering unit which performs rendering processing with respect to the input medical image, and a parameter determining unit which determines a parameter for execution of the rendering processing on the basis of the diagnosis information.

Preferably, the medical image comprises a two-dimensional image, and the apparatus further comprises a pixel data generating unit which generates pixel data by concatenating each pixel of the two-dimensional image while maintaining connectivity in a direction perpendicular to a cross section.

Preferably, the apparatus further comprises a keyword input unit which inputs a keyword for analysis of the diagnosis information, and the parameter determining unit determines a parameter for execution of the rendering processing from the keyword and the pixel data.

Preferably, the parameter includes an opacity and color information corresponding to each CT value of a medical image and a line-of-sight direction in generating a three-dimensional image, and is selected from a table storing initial values thereof in advance by the parameter determining unit.

Preferably, the apparatus further comprises an optimizing unit which optimizes the parameter for the medical image.

Preferably, the rendering unit executes shading processing and ray casting processing for the pixel data, the shading processing being performed to obtain color information and a shading value for the optimized pixel data, and the ray casting processing being performed to generate a rendering image in a line-of-sight direction on the basis of an opacity and a shading value which are assigned to the pixel data and an intensity of incident light.

According to the present invention, there is provided a reporting system which outputs an image selected by one of the image processing apparatuses described above or an image having undergone rendering processing by one of the image processing apparatuses.

According to the present invention, there is provided an image processing method comprising an image input step of inputting a plurality of medical images obtained by imaging, an information input step of inputting diagnosis information associated with the input medical images, a search step of searching the medical images for a morbid region on the basis of the diagnosis information, and a selecting step of selecting a medical image including the found morbid region from the plurality of medical images.

Preferably, the method further comprises a keyword input step of inputting a keyword for analysis of the diagnosis information, and a parameter determining step of determining a parameter for execution of a search in the search step from the keyword and the diagnosis information.

Preferably, the parameter includes at least one of each CT value/MRI value range for a medical image, each CT value/MRI value range which designates a lesion, and a slice position, and is selected from a table storing initial values thereof in the parameter determining step.

Preferably, the apparatus further comprises an optimizing step of optimizing the parameter for the medical image.

According to the present invention, there is provided an image processing method comprising an image input step of inputting a plurality of medical images obtained by imaging, an information input step of inputting diagnosis information associated with the input medical images, a rendering step of performing rendering processing with respect to the input medical image, and a parameter determining step of determining a parameter for execution of the rendering processing on the basis of the diagnosis information.

Preferably, the medical image comprises a two-dimensional image, and the method further comprises a pixel data generating step of generating pixel data by concatenating each pixel of the two-dimensional image while maintaining connectivity in a direction perpendicular to a cross section.

Preferably, the method further comprises a keyword input step of inputting a keyword for analysis of the diagnosis information, and in the parameter determining step, a parameter for execution of the rendering processing is determined from the keyword and the pixel data.

Preferably, the parameter includes an opacity and color information corresponding to each CT value of a medical image and a line-of-sight direction in generating a three-dimensional image, and is selected from a table storing initial values thereof in advance in the parameter determining step.

Preferably, the method further comprises an optimizing step of optimizing the parameter for the medical image.

Preferably, in the rendering step, shading processing and ray casting processing are executed for the pixel data, the shading processing being performed to obtain color information and a shading value for the optimized pixel data, and the ray casting processing being performed to generate a rendering image in a line-of-sight direction on the basis of an opacity and a shading value which are assigned to the pixel data and an intensity of incident light.

According to the present invention, there is provided a reporting method which outputs an image selected by any one of the image processing methods described above or an image having undergone rendering processing by any one of the image processing methods described above with the image being attached to the diagnosis information.

In order to execute the functions of the above image processing method, the present invention may take the form of a program comprising a code for an image input step of inputting a plurality of medical images obtained by imaging, a code for an information input step of inputting diagnosis information associated with the input medical images, a code for a search step of searching the medical images for a morbid region on the basis of the diagnosis information, and a code for a selecting step of selecting a medical image including the found morbid region from the plurality of medical images, or a computer-readable storage medium storing the program.

In order to execute the functions of the above image processing method, the present invention may take the form of a program comprising a code for an image input step of inputting a plurality of medical images obtained by imaging, a code for an information input step of inputting diagnosis information associated with the input medical images, a code for a rendering step of performing rendering processing with respect to the input medical image, and a code for a parameter determining step of determining a parameter for execution of the rendering processing on the basis of the diagnosis information, or a computer-readable storage medium storing the program.

As described above, according to the present invention, a large amount of images can be searched for a morbid region on the basis of diagnosis information, and an image or images including the morbid region can be selected.

A parameter in executing rendering processing for an image is determined on the basis of diagnosis information, and an image or images including a morbid region can be generated from this parameter.

In addition, a reporting system and reporting method can be constructed, which can output an image selected by the above image processing or an image having undergone rendering processing by the image processing, as a diagnosis report, with the image being attached to diagnosis information.

Other objects and advantages besides those discussed above shall be apparent to those skilled in the art from the description of a preferred embodiment of the invention which follows. In the description, reference is made to accompanying drawings, which form a part thereof, and which illustrate an example of the invention. Such example, however, is not exhaustive of the various embodiments of the invention, and therefore reference is made to the claims which follow the description for determining the scope of the invention.

DETAILED DESCRIPTION OF THE PREFERRED EMBODIMENTS

The preferred embodiments of the present invention will be described below with reference to the accompanying drawings.

First Embodiment

Figure 1:
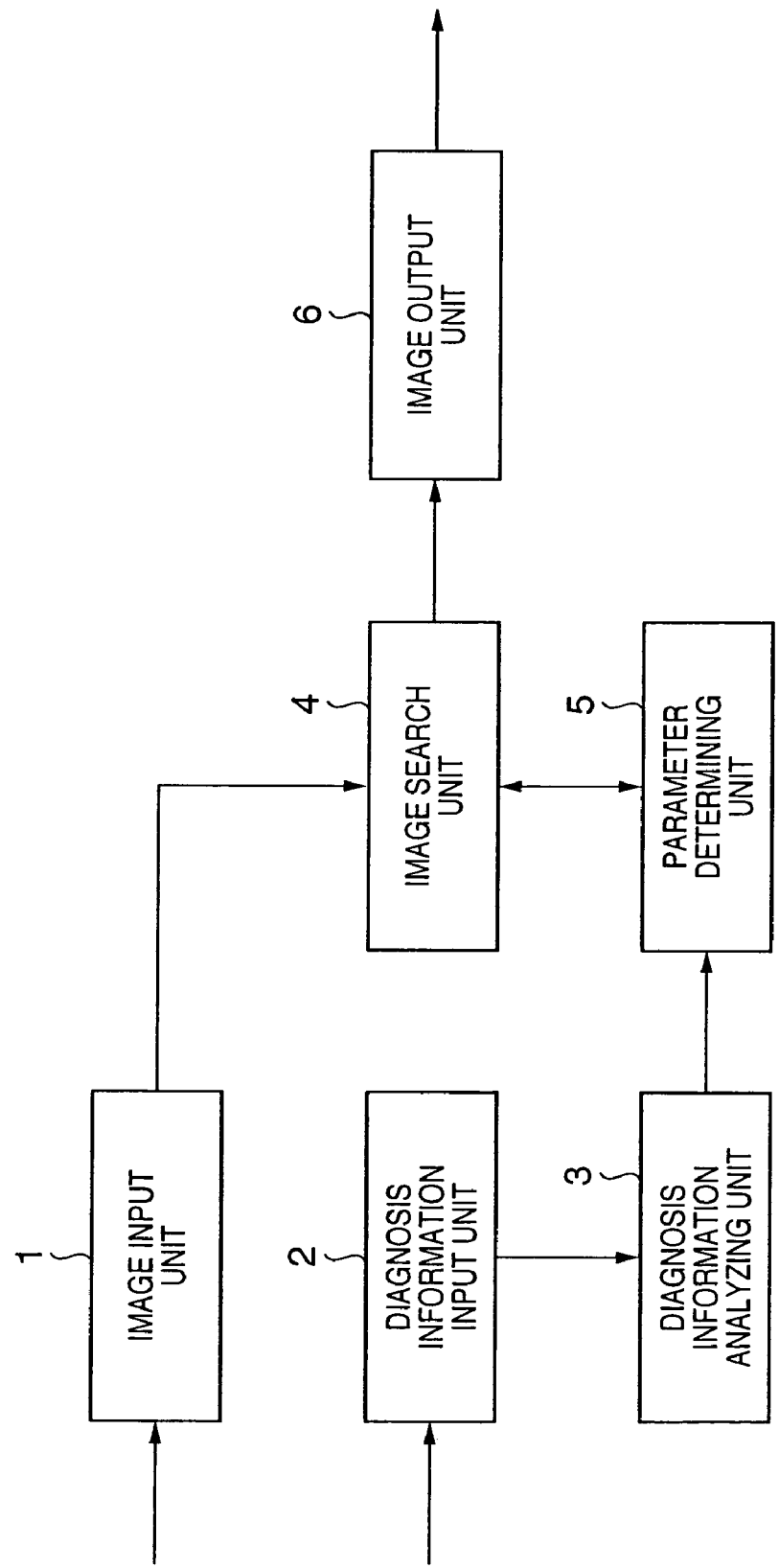
FIG. 1 is a view schematically showing function blocks constituting an image processing apparatus according to the first embodiment of the present invention.

FIG. 1 schematically shows function blocks constituting an image processing apparatus according to the first embodiment of the present invention. An image search unit 4 searches all image data obtained by imaging which are input from an image input unit 1 for a morbid region as an output target on the basis of diagnosis information, and outputs an image or images obtained by imaging which correspond to the morbid region as a key image or key images from an image output unit 6.

The image input unit 1 may be a medical imaging apparatus such as a CT or MRI apparatus or may be an image input interface and an accompanying storage device to which data is input from such an apparatus through a network.

A diagnosis information input unit 2 receives a diagnosis result as diagnosis information (to be also referred to as a diagnosis report hereinafter) which is obtained by a doctor (e.g., a radiologist) using image data obtained by imaging. This diagnosis report is input in the form of, for example, text information or voice information. Note that the diagnosis result is output to a display device (not shown). In addition to the diagnosis made by the doctor, a diagnosis result obtained by using a computer, a diagnosis result directly obtained by using an imaging film, and the like can be used.

The diagnosis information input from the diagnosis information input unit 2 is subjected to a keyword search in a diagnosis information analyzing unit 3. In this keyword search, anatomical and pathological terms are extracted in association with each other.

The above anatomical terms include the right frontal lobe, left lung, liver, and the like. The pathological terms include growth, embolization, and node, stages I, II, and III indicating the progression degrees of diseases, and the like.

A keyword can be input to the diagnosis information input unit 2. In this case, there is no need to input a keyword to the diagnosis information analyzing unit 3.

A parameter determining unit 5 calculates parameters used in the image search unit 4 on the basis of the input keyword.

The above parameters include a CT or MRI value range as an anatomical threshold, a CT or MRI value range which designates a lesion, a slice position, and the like. These initial values are selected from a table empirically determined in advance in consideration of the progression degrees of diseases, but vary among individuals.

In order to correct (optimize) the variations, each selected parameter is applied to an input image to determine the optimization degree of the parameter.

This optimization degree can be determined depending on how the area or connectivity of a found morbid region changes within a cross section or between cross sections as the parameter is changed. In extracting a lung, for example, when air is insufficiently inhaled, the CT value of the lung may be measured higher than the actual value.

If a normal CT value range is applied to such an image, the area of the lung field becomes extremely smaller than the cross-sectional area of the chest portion. Therefore, the CT value is corrected to set a proper ratio (about 50 to 60%).

In general, the area of the lung field gradually decreases toward the lower portion of the lung. In some rare cases, however, intestinal gas is detected as a lung field.

Such gas can be eliminated by a regional restriction within the CT value range restriction on the basis of the connectivity conditions for the lung field from the middle lobe.

With the above determination, a region of the target organ in the image is limited.

When the boundary of the target organ is determined, a morbid region inside the boundary is extracted.

As a means for extracting a morbid region from the image, a computer-aided diagnosis technique studied as a diagnosis support technique and disclosed in (Toshiaki Okumura, Tomoko Miwa, Fumihiro Okumoto, Nobuaki Masuto, Shinji Yamamoto, Mitsuomi Matsumoto, Yukio Tateno, Takeshi Iinuma, and Tohru Matsumoto, "Diagnosis Support System for Lung Cancer Screening CT (LSCT)", Journal of Computer Aided Diagnosis of Medical Images, Vol. 2, No. 3, 1998) is used.

In this embodiment, one of the lesion candidates detected by this computer aided diagnosis technique is selected, which coincides with the final diagnosis by the doctor.

The parameter determining unit 5 determines a slice position including the finally detected lesion. In general, there are a plurality of slices (cross sections) including the lesion. Therefore, all these cross sections are found as key images by the image search unit 4.

The image search unit 4 may subsample cross sections exhibiting small changes in the area or shape of the lesion.

The key image found by the image search unit 4 is output to the image output unit 6. The image is then output from the image output unit 6 to a display device, network computer, or the like. Note that the information output to the image output unit 6 may be the key image alone or the key image with diagnosis information attached.

Figure 2:
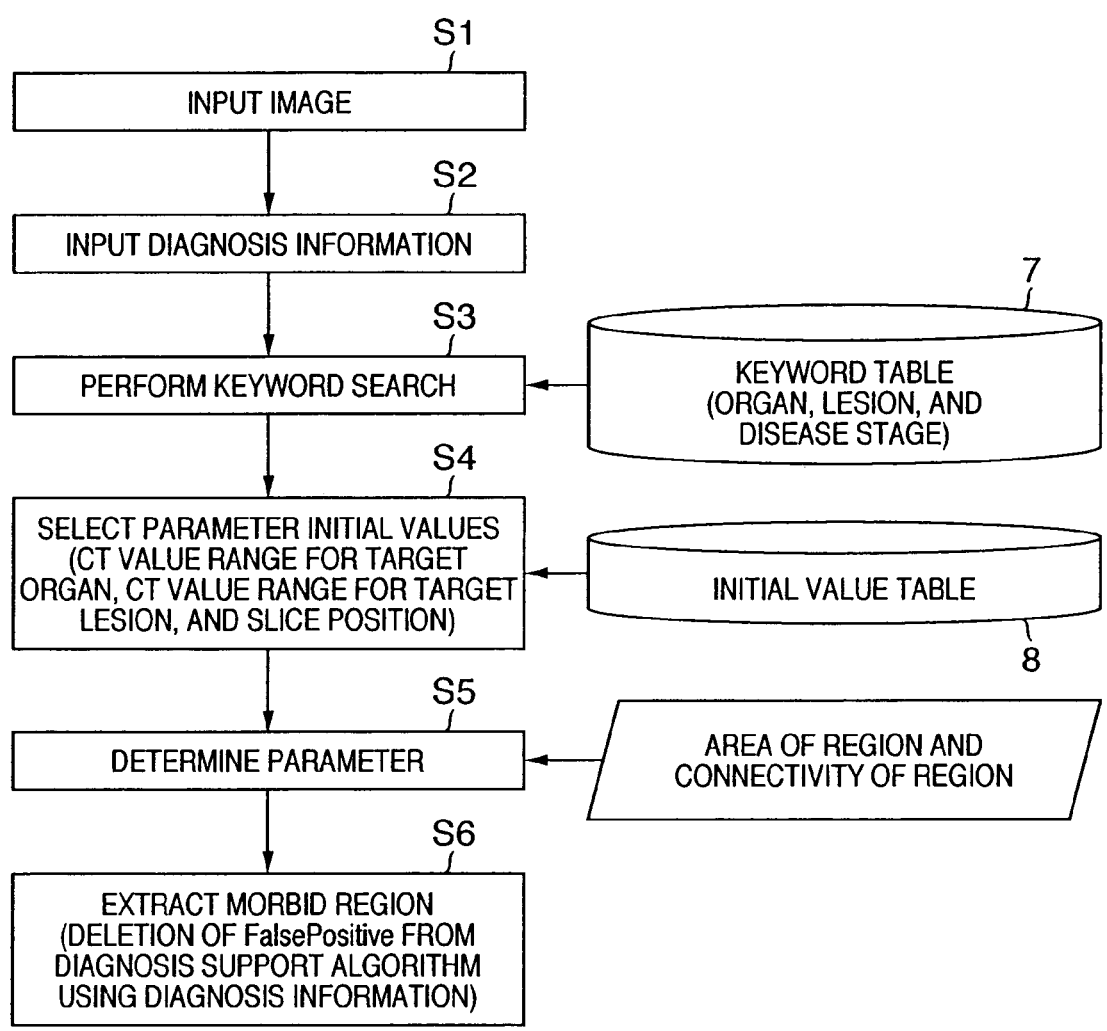
FIG. 2 is a flowchart showing image processing in the first embodiment.

FIG. 2 is a flowchart showing image processing in the first embodiment.

As shown in FIG. 2, in step S1, image data obtained by imaging is input to the image input unit 1 serving as a medical imaging apparatus such as a CT or MRI apparatus, an image input interface and an accompanying storage device to which data is input from such an apparatus through a network.

In step S2, the diagnosis result obtained by the doctor using the image data obtained by imaging is input as diagnosis information to the diagnosis information input unit 2.

In step S3, a keyword table 7 is searched for the keyword input to the diagnosis information input unit 2 or diagnosis information analyzing unit 3.

In step S4, the parameter determining unit 5 selects an initial value parameter used in the image search unit 4 from an initial value table 8 on the basis of the input keyword.

In steps S5 and S6, the image search unit 4 applies the selected parameter to the input image to determine the optimization degree of the parameter on the basis of the area or connectivity of the morbid region (optimization), and extracts the morbid region by using a general computer aided diagnosis technique.

Thereafter, one of the lesion candidates detected by the computer aided diagnosis technique is selected, which coincides with the final diagnosis by the doctor.

Second Embodiment

Figure 3:
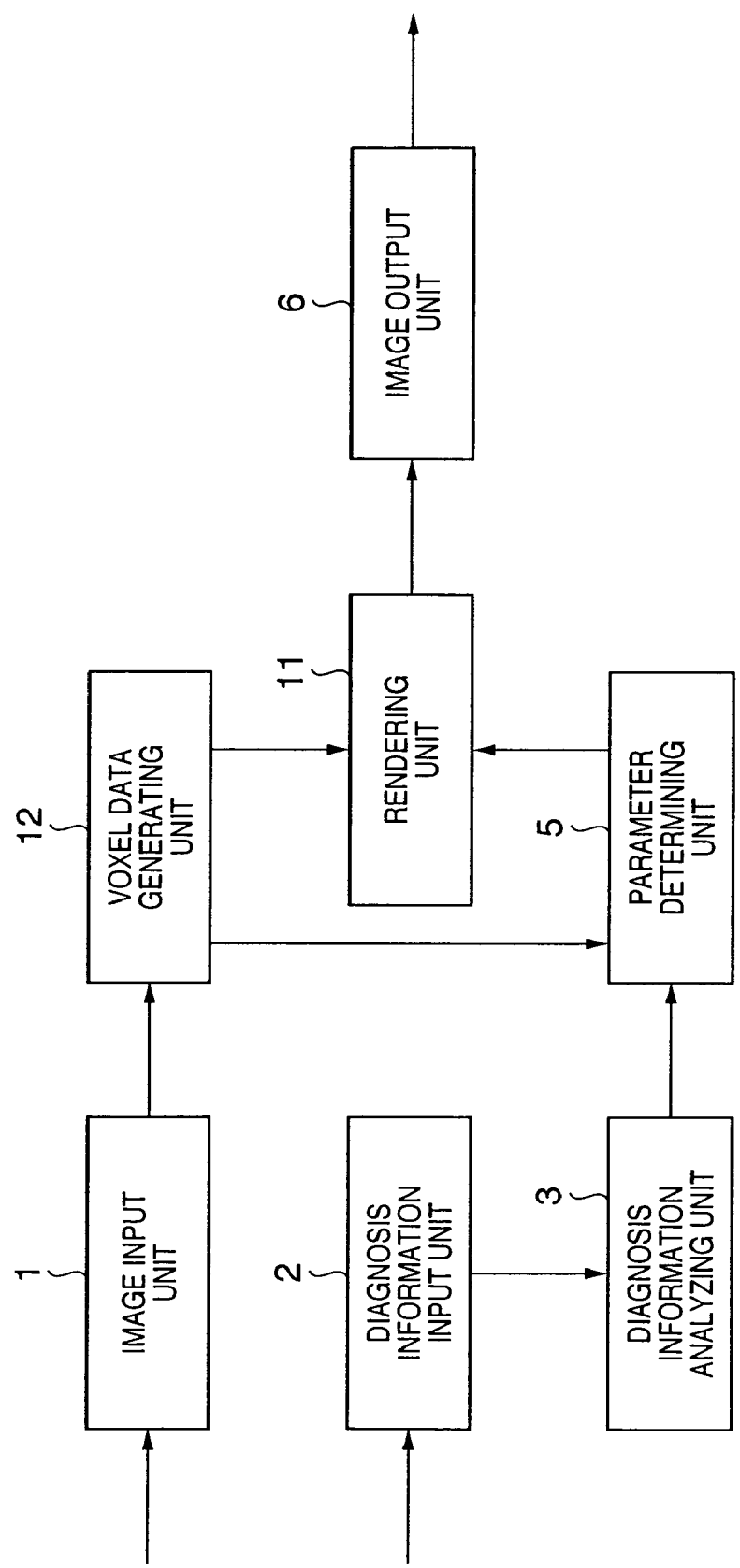
FIG. 3 is a view schematically showing function blocks constituting an image processing apparatus according to the second embodiment of the present invention.

FIG. 3 schematically shows function blocks constituting an image processing apparatus according to the second embodiment of the present invention. The second embodiment differs from the first embodiment in that a rendering unit 11 and voxel data generating unit 12 are provided in place of the image search unit 4, a parameter determining unit 5 determines parameters such as an opacity and color (a density value in the case of a halftone image) for three-dimensional rendering executed by the rendering unit 11 on the basis of diagnosis information as in the first embodiment, and the resultant rendering image is used as a key image.

Other elements are the same as those in the first embodiment. Therefore, the same reference numerals denote the same elements, and a description thereof will be omitted.

When a plurality of CT or MRI images are input to an image input unit 1, the voxel data generating unit 12 generates voxel data. The voxel data is generated by concatenating two-dimensional images in the Z-axis direction in consideration of the continuity of pixels.

A three-dimensional rendering image can be obtained by assigning an opacity and color to each pixel of this pixel data and using, for example, a volume rendering technique.

This embodiment uses the volume rendering technique. However, a three-dimensional image may be formed by a surface rendering method of performing shading at the surface boundary, detected with the threshold selected by the parameter determining unit 5, by using gray level gradient method of reflecting a three-dimensional density gradient in shading operation.

With the diagnosis information input to a diagnosis information input unit 2, a diagnosis information analyzing unit 3 performs a keyword search by referring to a keyword table 7 as in the first embodiment.

The parameter determining unit 5 selects an opacity and color information, each corresponding to each CT value, and a line-of-sight direction in the generation of a three-dimensional image from an initial value table 8 in correspondence with the anatomical region, pathological information, and disease stage found by the keyword search. Basically, volume rendering is executed by the rendering unit 11 using these set values determined in advance.

In order to clearly express the boundary between an organ and a lesion, segmentation is preferably performed. That is, in some cases, the boundary between the lung or liver or growth existing in such an organ cannot be smoothly reproduced by using a predetermined opacity and color information corresponding to each CT value.

For this reason, a CT value range is converged by observing the connectivity of binary images, obtained with different CT value thresholds, within a cross section or between cross sections. Isolated regions generated in binarization within the converged CT value range are removed by labeling. This makes it possible to extract an organ and lesion more smoothly.

Assigning a new opacity and color information to each pixel constituting an organ and lesion in an image segmented in the above manner can obtain a smooth three-dimensional image.

The rendering unit 11 includes the functions of a shading step and ray casting step. In the shading step, the gradient of a normal vector is calculated with respect to each pixel (voxel) of a segmented organ and lesion. The product (shading value) of color information and the gradient of the normal vector is then obtained. In this case, a gradient is calculated from two points on each axis at a target point, which provide a total of six neighboring points.

In the ray casting step, a rendering image is generated from the integration of voxel values in the line-of-sight direction on the basis of the opacity and shading value assigned to each voxel and the intensity of incident light. Optical attenuation computation is also performed at this point of time. The line-of-sight direction used at this time is also an important determination parameter.

In some cases, an observation direction is diagnostically determined. If, however, a growth or the like exists on the back side of the human body, it is obvious that observation from the back side facilitates observation.

That is, the parameter determining unit 5 also selects, as a line-of-sight direction, a direction in which the distance from an organ surface of body surface to a lesion such as a growth is short. If there are a plurality of directions in which the distances to the lesion are the same, a three-dimensional image is generated from the plurality of directions and output.

The three-dimensional image generated by the rendering unit 11 is output to an image output unit 6. The image output unit 6 then outputs the image to a display device, network computer, or the like. Note that the information output to the image output unit 6 may be the rendering image alone or the rendering image with diagnosis information attached.

Figure 4:
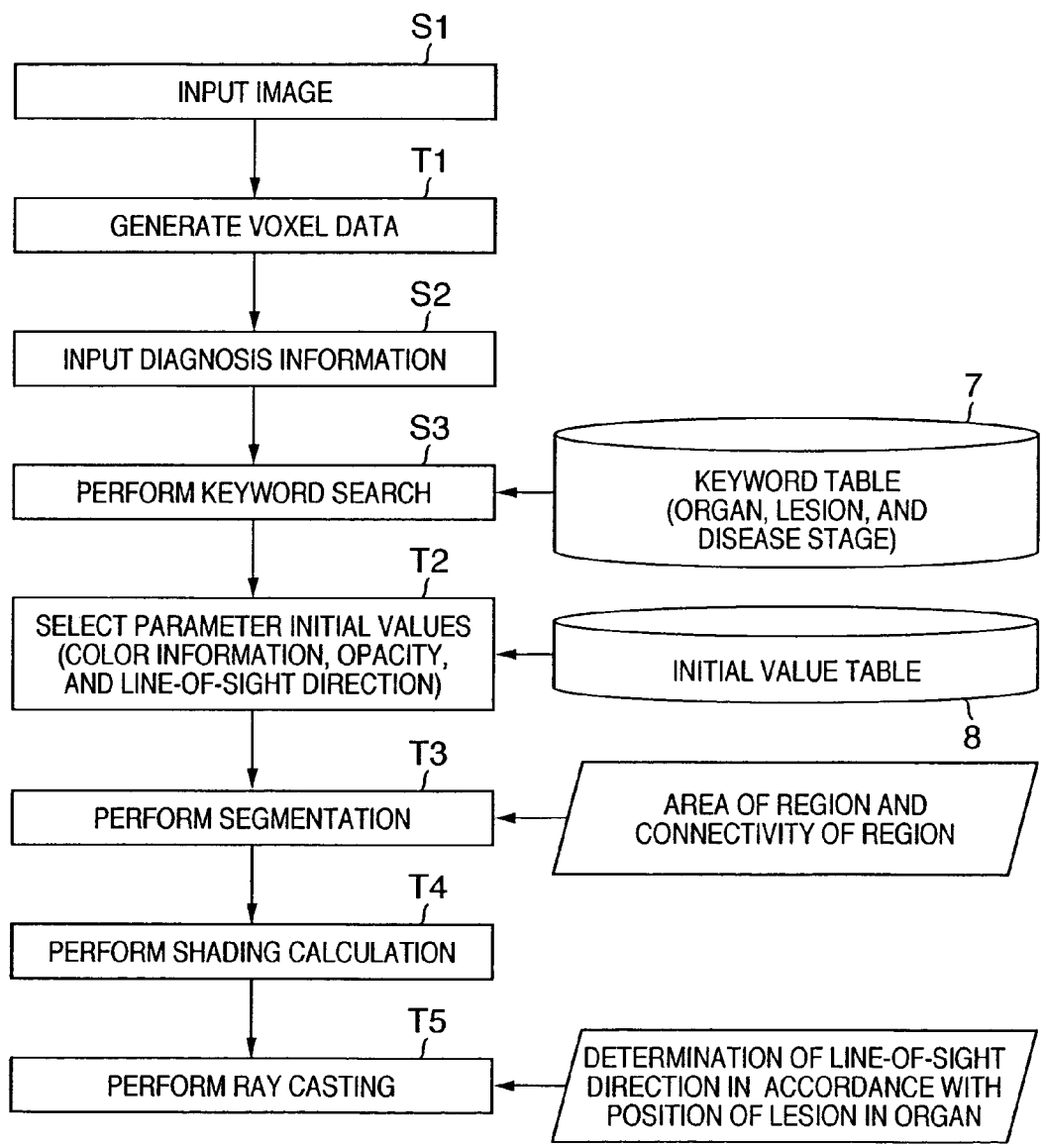
FIG. 4 is a flowchart showing image processing in the second embodiment.

FIG. 4 is a flowchart showing image processing in the second embodiment.

As shown in FIG. 4, in step S1, image data obtained by imaging is input to the image input unit 1 serving as a medical imaging apparatus such as a CT or MRI apparatus, an image input interface and an accompanying storage device to which data is input from such an apparatus through a network.

In step T1, the voxel data generating unit 12 generates voxel data from the above image data obtained by imaging.

In step S2, the diagnosis result obtained by the doctor using the image data obtained by imaging is input as diagnosis information to the diagnosis information input unit 2.

In step S3, the keyword table 7 is searched for the keyword input to the diagnosis information input unit 2 or diagnosis information analyzing unit 3.

In step T2, the parameter determining unit 5 selects initial value parameters such as an opacity and line-of-sight direction in three-dimensional rendering executed by the rendering unit 11 from the initial value table 8 on the basis of the input keyword.

In step T3, the rendering unit 11 applies the selected parameters to the input image, and executes segmentation (optimization) on the basis of the area of a morbid region, its change, and connectivity, in order to clearly express the boundary between the organ and the lesion.

In step T4, the rendering unit 11 calculates the gradient of a normal vector with respect to each voxel of the segmented organ and lesion, and obtains the product (shading value) of color information and the gradient of the normal vector (shading).

In step T5, a rendering image is generated from the integration of voxel values in the line-of-sight direction on the basis of the opacity and shading value assigned to each voxel and the intensity of incident light (ray casting).

The second embodiment has exemplified the case-of the use of the volume rendering technique. This three-dimensional image generating technique has been widely studied, other than medical image applications, and there are many books of reference. For example, see Takeshi Agui et al., "Future Image Information Series 5, Computer Graphics", Chapter 7, Shokodo.

According to the first and second embodiments, proper key images with a small amount/small volume of data can be selected or generated from a large amount of images obtained by imaging on the basis of a large amount of medical information and doctor's diagnosis information (the forms of an organ including a lesion and the lesion and the progression degree of a disease).

In addition, a slice image accurately expressing disease information can be designated from many slice images by using diagnosis information.

Furthermore, a three-dimensional image accurately expressing a morbid region can be generated as a key image data with a small amount/small volume of data by using the same technique.

In determining a line-of-sight direction at the time of the generation of a key image, a direction in which the distance from an organ or body surface to a lesion is short is selected. This facilitates observation of a morbid region.

Furthermore, a reporting system and reporting method can be constructed, which can output a diagnosis report upon attaching, to diagnosis information, an image selected by the above image processing or an image having undergone rendering processing in the above image processing.

Other Embodiment

The present invention incorporates a case wherein programs of software (the codes of the respective steps in the flowcharts of FIGS. 2 and 4) for implementing the functions of the embodiments described above are directly or remotely supplied to a system or apparatus to cause the computer of the system or apparatus to read out and execute the programs, thereby implementing the functions. In this case, the form of the present invention need not be programs as long as it has the functions of the programs.

The program codes themselves which are installed in the computer to allow the computer to implement the functions/processing of the present invention also realize the present invention. That is, the computer programs themselves, which implement the functions/processing of the present invention, are also incorporated in the claims of the present invention.

In this case, each program may take any form, such as an object code, a program executed by an interpreter, and script data supplied to an OS, as long as it has the function of the program.

As a recording medium for supplying the programs, a flexible disk, hard disk, optical disk, magnetooptical disk, MO, CD-ROM, CD-R, CD-RW, magnetic tape, nonvolatile memory card, ROM, DVD (DVD-ROM or DVD-R), or the like can be used.

In addition, methods of supplying the programs include the following. A client computer connects to a home page on the Internet by using a browser to download each computer program of the present invention itself from the home page or download a compressed file containing an automatic install function into a recording medium such as a hard disk. Alternatively, the programs can be supplied by dividing the program codes constituting each program of the present invention into a plurality of files, and downloading the respective files from different home pages. That is, the claims of the present invention also incorporate a WWW server which allows a plurality of users to download program files for causing the computer to execute the functions/processing of the present invention.

In addition, the functions/processing of the present invention can be implemented by encrypting the programs of the present invention, storing the encrypted data in storage media such as CD-ROMs, distributing them to users, allowing users who satisfy a predetermined condition to download key information for decryption from a home page through the Internet, executing the encrypted programs using the key information, and allowing a computer to install the programs.

The functions of the above embodiments are implemented not only when the readout programs are executed by the computer but also when the OS running on the computer performs part or all of actual processing on the basis of the instructions of the programs.

The functions of the above embodiments are also implemented when the programs read out from the storage medium are written in the memory of a function expansion board inserted into the computer or a function expansion unit connected to the computer, and the CPU of the function expansion board or function expansion unit performs part or all of actual processing on the basis of the instructions of the programs.

The present invention is not limited to the above embodiments and various changes and modifications can be made within the spirit and scope of the present invention. Therefore, to apprise the public of the scope of the present invention, the following claims are made.

What is claimed is:

1. An image processing apparatus comprising:
    an image input unit which inputs a plurality of medical images obtained by imaging;
    an information input unit which inputs diagnosis information associated with the input medical images;
    a rendering unit which performs rendering processing with respect to the input medical image;
    a parameter determining unit which determines a parameter for execution of the rendering processing on the basis of the diagnosis information, and
    an optimizing unit which optimizes the parameter for the medical image,
    wherein the medical image comprises a two-dimensional image, and the apparatus further comprises a pixel data generating unit which generates pixel data by concatenating each pixel of the two-dimensional image while maintaining connectivity in a direction perpendicular to a cross section,
    wherein the apparatus further comprises a keyword input unit which inputs a keyword for analysis of the diagnosis information, and said parameter determining unit determines a parameter for execution of the rendering processing from the keyword and the pixel data,
    wherein the parameter includes an opacity and color information corresponding to each CT value of a medical image and a line-of-sight direction in generating a three-dimensional image, and is selected from a table storing initial values thereof in advance by said parameter determining unit, and
    wherein said rendering unit executes shading processing and ray casting processing for the pixel data, the shading processing being performed to obtain color information and a shading value for the optimized pixel data, and the ray casting processing being performed to generate a rendering image in a line-of-sight direction on the basis of an opacity and a shading value which are assigned to the pixel data and an intensity of incident light.

2. A reporting system which outputs an image having undergone rendering processing by an image processing apparatus defined in claim 1 with the image being attached to the diagnosis information.

3. An image processing method comprising:
    an image input step of inputting a plurality of medical images obtained by imaging;
    an information input step of inputting diagnosis information associated with the input medical images;
    a rendering step of performing rendering processing with respect to the input medical image;
    a parameter determining step of determining a parameter for execution of the rendering processing on the basis of the diagnosis information, and
    an optimizing step of optimizing the parameter for the medical image,
    wherein the medical image comprises a two-dimensional image, and the method further comprises a pixel data generating step of generating pixel data by concatenating each pixel of the two-dimensional image while maintaining connectivity in a direction perpendicular to a cross section, wherein the method further comprises a keyword input step of inputting a keyword for analysis of the diagnosis information, and in the parameter determining step, a parameter for execution of the rendering processing is determined from the keyword and the pixel data, wherein the parameter includes an opacity and color information corresponding to each CT value of a medical image and a line-of-sight direction in generating a three-dimensional image, and is selected from a table storing initial values thereof in advance in the parameter determining step, wherein in the rendering step, shading processing and ray casting processing are executed for the pixel data, the shading processing being performed to obtain color information and a shading value for the optimized pixel data, and the ray casting processing being performed to generate a rendering image in a line-of-sight direction on the basis of an opacity and a shading value which are assigned to the pixel data and an intensity of incident light.

4. A reporting method which outputs an image having undergone rendering processing by an image processing method defined in claim 3 with the image being attached to the diagnosis information.

* * * * *